(12) United States Patent
Suzuki et al.

(10) Patent No.: US 10,693,080 B2
(45) Date of Patent: Jun. 23, 2020

(54) SOLVENT FOR PRODUCING ORGANIC TRANSISTOR

(71) Applicant: DAICEL CORPORATION, Osaka-shi, Osaka (JP)

(72) Inventors: Youji Suzuki, Himeji (JP); Takeshi Yokoo, Himeji (JP); Yasuyuki Akai, Himeji (JP)

(73) Assignee: DAICEL CORPORATION, Osaka-Shi (JP)

( * ) Notice: Subject to any disclaimer, the term of this patent is extended or adjusted under 35 U.S.C. 154(b) by 100 days.

(21) Appl. No.: 15/033,787

(22) PCT Filed: Nov. 13, 2014

(86) PCT No.: PCT/JP2014/080031
§ 371 (c)(1),
(2) Date: May 2, 2016

(87) PCT Pub. No.: WO2015/076171
PCT Pub. Date: May 28, 2015

(65) Prior Publication Data
US 2016/0293849 A1 Oct. 6, 2016

(30) Foreign Application Priority Data
Nov. 21, 2013 (JP) ................. 2013-241096

(51) Int. Cl.
| | | |
|---|---|---|
| *H01L 51/00* | (2006.01) | |
| *C07C 211/35* | (2006.01) | |
| *C07D 307/79* | (2006.01) | |
| *H01L 51/05* | (2006.01) | |
| *C08G 61/12* | (2006.01) | |
| *C09D 165/00* | (2006.01) | |
| *C07C 49/403* | (2006.01) | |
| *C07C 43/184* | (2006.01) | |
| *C07C 43/205* | (2006.01) | |

(52) U.S. Cl.
CPC ........ *H01L 51/0068* (2013.01); *C07C 43/184* (2013.01); *C07C 43/205* (2013.01); *C07C 43/2055* (2013.01); *C07C 49/403* (2013.01); *C07C 211/35* (2013.01); *C07D 307/79* (2013.01); *C08G 61/124* (2013.01); *C08G 61/126* (2013.01); *C09D 165/00* (2013.01); *H01L 51/0007* (2013.01); *H01L 51/0072* (2013.01); *H01L 51/0558* (2013.01); *C07C 2601/14* (2017.05); *C08G 2261/1412* (2013.01); *C08G 2261/3223* (2013.01); *C08G 2261/3327* (2013.01); *C08G 2261/344* (2013.01); *C08G 2261/92* (2013.01)

(58) Field of Classification Search
CPC ..................................... H01B 1/124
See application file for complete search history.

(56) References Cited

U.S. PATENT DOCUMENTS

| | | | |
|---|---|---|---|
| 2003/0099774 A1 | 5/2003 | Morii et al. | |
| 2006/0045959 A1* | 3/2006 | Yasukawa | C09D 11/30 427/66 |
| 2009/0302311 A1 | 12/2009 | Turbiez et al. | |
| 2010/0270542 A1 | 10/2010 | Zhu | |
| 2012/0059140 A1 | 3/2012 | Hayoz et al. | |

(Continued)

FOREIGN PATENT DOCUMENTS

| | | |
|---|---|---|
| CN | 103140492 A | 6/2013 |
| CN | 103304780 A | 9/2013 |

(Continued)

OTHER PUBLICATIONS

Taiwanese Notification for the Opinion of Examination and Search Report, dated Apr. 12, 2018, for Taiwanese Application No. 103140168, along with English translations.
Chinese Office Action, dated Aug. 14, 2018, for Chinese Application No. 201480057473.3, along with an English translation.
Chen et al., "Highly π-Extended Copolymers with Diketopyrrolopyrrole Moieties for High-Performance Field-Effect Transistors", Advanced Materials, 2012, vol. 24, pp. 4618-4622.
International Search Report for PCT/JP2014/080031 dated Feb. 24, 2015.
Lei et al., "Influence of Alkyl Chain Branching Positions on the Hole Mobilities of Polymer Thin-Film Transistors", Advanced Materials, 2012, vol. 24, pp. 6457-6461.

(Continued)

*Primary Examiner* — William D Young
(74) *Attorney, Agent, or Firm* — Birch, Stewart, Kolasch & Birch, LLP

(57) ABSTRACT

Provided is a solvent for organic transistor production. The solvent has excellent solubility for organic semiconductor materials and enables formation of an organic transistor having high crystallinity. The solvent according to the present invention for organic transistor production includes a solvent A represented by Formula (a). In the formula, Ring Z represents a ring selected from an aromatic carbon ring, a 5- to 7-membered alicyclic carbon ring, and a 5- to 7-membered heterocyclic ring; $R^1$ represents a group selected from oxo, thioxy, $-OR^a$, $-SR^a$, $-O(C=O)R^a$, $-R^bO(C=O)R^a$, and substituted or unsubstituted amino; and $R^2$ represents a group selected from hydrogen, $C_1$-$C_7$ alkyl, aryl, and $-OR^a$, where $R^1$ and $R^2$ may be linked to each other to form a ring with one or more carbon atoms constituting Ring Z.

[Chem. 1]

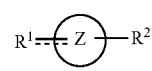

(a)

4 Claims, No Drawings

(56) References Cited

U.S. PATENT DOCUMENTS

| | | | |
|---|---|---|---|
| 2013/0240792 A1* | 9/2013 | Wigglesworth | H01L 51/0036 252/500 |
| 2014/0303335 A1 | 10/2014 | Hayoz et al. | |
| 2016/0049589 A1 | 2/2016 | Turbiez et al. | |
| 2017/0005270 A1 | 1/2017 | Hayoz et al. | |

FOREIGN PATENT DOCUMENTS

| | | |
|---|---|---|
| EP | 2 232 606 A | 9/2010 |
| JP | 2003-238286 A | 8/2003 |
| JP | 2004-88094 A | 3/2004 |
| JP | 2006-66294 A | 3/2006 |
| JP | 2009-541548 A | 11/2009 |
| JP | 2011-508967 A | 3/2011 |
| JP | 2012-28180 A | 2/2012 |
| JP | 2012-521462 A | 9/2012 |
| WO | WO 2009/079150 A1 | 6/2009 |
| WO | 2012/041849 A1 | 4/2012 |
| WO | WO 2012/084757 A1 | 6/2012 |
| WO | WO 2013/150005 A1 | 10/2013 |
| WO | WO 2014/136436 A1 | 9/2014 |

OTHER PUBLICATIONS

Written Opinion of the International Searching Authority for PCT/JP2014/080031 (PCT/ISA/237) dated Feb. 24, 2015.

Japanese Notification of Reasons for Refusal, dated Oct. 30, 2018, for Japanese Application No. 2015-549092, with an English translation.

* cited by examiner

SOLVENT FOR PRODUCING ORGANIC TRANSISTOR

TECHNICAL FIELD

The present invention relates to a solvent that is used for organic transistor production and has excellent solubility for organic semiconductor materials; and to a composition that is used for organic transistor production and includes an organic semiconductor material and the solvent for organic transistor production. The present application claims priority to Japanese Patent Application No. 2013-241096 filed to Japan Nov. 21, 2013, the entire contents of which are incorporated herein by reference.

BACKGROUND ART

Organic transistors are widely used as principal semiconductor electronic devices constituting displays and computer devices, and are now produced using inorganic substances, such as polysilicon and amorphous silicon, as semiconductor materials. Disadvantageously, production of thin-film organic transistors using such inorganic substances requires a vacuum process and/or a high-temperature process and causes increased production costs. In addition, the presence of the high-temperature process in the production imposes limitations on substrates that are usable. The substrate to be used in the production has been selected mainly typically from glass substrates. However, the glass substrates, although having good heat resistance, are susceptible to impact, hardly achieve weight reduction, have poor flexibility, and hardly give flexible organic transistors.

As a possible solution to this issue, organic electronic devices using organic semiconductor materials have been studied and developed actively through the years. Advantageously, the organic semiconductor materials can easily form thin films by a simple procedure via a wet process such as printing process or spin coating process and allow the production process to proceed at a lower temperature as compared with the conventional organic transistors using inorganic semiconductor materials. This enables the formation of thin films on plastic substrates, which generally have low heat resistance, and achieves reduction in weight and cost of electronic devices such as displays. In addition, such organic electronic devices are expected to be used in broader, various ways such as uses utilizing the flexibility of the plastic substrates.

When used as the organic semiconductor materials, low-molecular-weight semiconductor materials such as pentacene are known to develop semiconductor device performance at high level. However, most of unsubstituted acene compounds typified by pentacene have poor solubility in common solvents, due to strong intermolecular interaction by the π-conjugated system. The poor solubility impedes the preparation of a high-concentration composition for organic transistor production, but gives a low-concentration composition. The resulting organic semiconductor, when formed by printing process using such a low-concentration composition has smaller crystal grains. Typically disadvantageously, the organic semiconductor is not energized unless a high voltage is applied, and the application of such a high voltage causes the insulating film to be separated.

In addition, Non Patent Literature (NPL) 1 and NPL 2 describe the use of donor-acceptor copolymer compounds having a thiophene skeleton as organic semiconductor materials. The compounds exhibit high mobilities due to strong π-π stacking and resulting high π-electron overlap. Disadvantageously, however, the strong π-π stacking causes the compounds to have high crystallinity and poor solubility in common solvents. The literature describes that the compounds are dissolved by heating using a halogenated solvent typified by 1,2-dichlorobenzene. However, resulting solutions of the compounds, when dissolved typically in 1,2-dichlorobenzene, often gelate at room temperature and are not suitable for thin film formation by a printing process. In addition, such halogenated solvents might cause ecological toxicity and offer working safety hazard.

CITATION LIST

Non Patent Literature

NPL 1: Adv. Mater. 2012, 24, pp. 4618-4622
NPL 2: Adv. Mater. 2012, 24, pp. 6457-6461

SUMMARY OF INVENTION

Technical Problem

Accordingly, the present invention has an object to provide a solvent for organic transistor production, where the solvent offers excellent solubility for organic semiconductor materials and can form an organic transistor having high crystallinity.

The present invention has another object to provide a composition for organic transistor production, where the composition contains the solvent for organic transistor production.

Solution to Problem

After intensive investigations to achieve the objects, the inventors of the present invention found that a specific solvent, when used, presents high solubility for organic semiconductor materials even at relatively low temperatures and enables the formation of an organic transistor by a printing process even on a plastic substrate, where the plastic substrate generally has lower heat resistance as compared with glass substrates. The inventors also found that a composition for organic transistor production containing the solvent and an organic semiconductor material, when applied onto a substrate, allows the organic semiconductor material to crystallize via self-assembly activity. In addition, the inventors found that the solvent, when combined with a solvent generally used for electron materials as needed, can have coatability and drying behavior at still higher levels. The present invention has been made based on these findings.

Specifically, the present invention provides a solvent for organic transistor production. The solvent is used for dissolving an organic semiconductor material and includes a solvent A represented by Formula (a):

[Chem. 1]

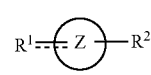

(a)

where Ring Z represents a ring selected from an aromatic carbon ring, a 5- to 7-membered alicyclic carbon ring, and a 5- to 7-membered heterocyclic ring; $R^1$ represents a group selected from oxo (=O), thioxy (=S), —$OR^a$, —$SR^a$, —O(C=O)R$^a$, —R$^b$O(C=O)R$^a$, and substituted or unsubstituted amino, where R$^a$ is selected from C$_1$-C$_7$ alkyl, aryl, and a group including two or more of these groups bonded to each other via a single bond or a linkage group, and R$^b$ is selected from C$_1$-C$_7$ alkylene, arylene, and a group including two or more of these groups bonded to each other via a single bond or a linkage group; and R$^2$ represents a group selected from hydrogen, C$_1$-C$_7$ alkyl, aryl, and —OR$^a$, where R$^a$ is as defined above, where R$^1$ and R$^2$ may be linked to each other to form a ring with one or more carbon atoms constituting Ring Z.

The solvent A in the solvent for organic transistor production may be at least one selected from the group consisting of 2-methylcyclopentanone, 2-methylcyclohexanone, cyclohexyl methyl ether, cyclohexylamine, methoxybenzene, 1,2-dimethoxybenzene, 2,3-dihydrobenzofuran, and 2,3-dihydro-3-methylbenzofuran.

The organic semiconductor material to be dissolved in the solvent for organic transistor production may be a compound including a constitutional unit represented by Formula (1):

[Chem. 2]

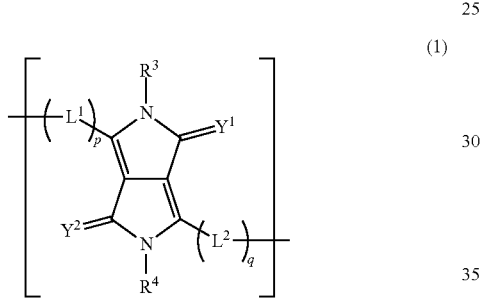

(1)

where L$^1$ and L$^2$ independently represent, identically or differently in each occurrence, a group selected from a group corresponding to an aromatic carbon ring or a heteroaromatic carbon ring, except for removing two hydrogen atoms therefrom, vinylene, ethynylene, and a divalent group including two or more of these groups in combination; R$^3$ and R$^4$ each represent, identically or differently, a group selected from hydrogen, optionally substituted C$_1$-C$_{24}$ alkyl, optionally substituted aryl, and optionally substituted heteroaryl; Y$^1$ and Y$^2$ are each, identically or differently, selected from oxygen and sulfur; p and q each represent, identically or differently, an integer of 0 or more, where the total of p and q is an integer of 1 or more. The "p" occurrences of L$^1$ may be identical or different, and the "q" occurrences of L$^2$ may be identical or different.

In the organic semiconductor material to be dissolved in the solvent for organic transistor production, L$^1$ and L$^2$ in Formula (1) may independently be, identically or differently in each occurrence, a group selected from groups represented by Formulae (L-1) to (L-22):

[Chem. 3]

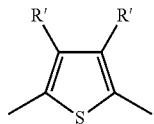

(L-1)

-continued

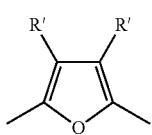

(L-2)

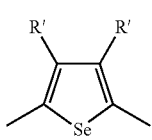

(L-3)

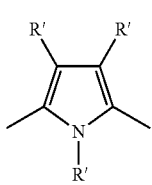

(L-4)

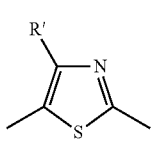

(L-5)

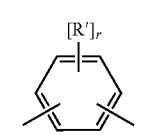

(L-6)

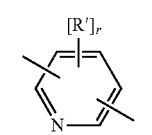

(L-7)

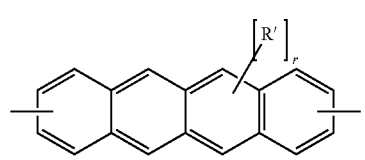

(L-8)

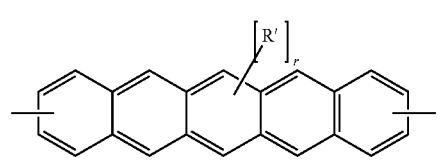

(L-9)

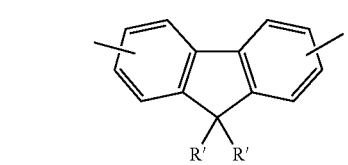

(L-10)

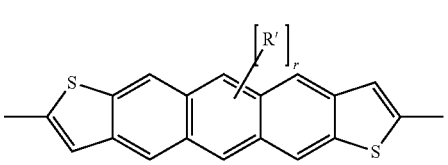

(L-11)

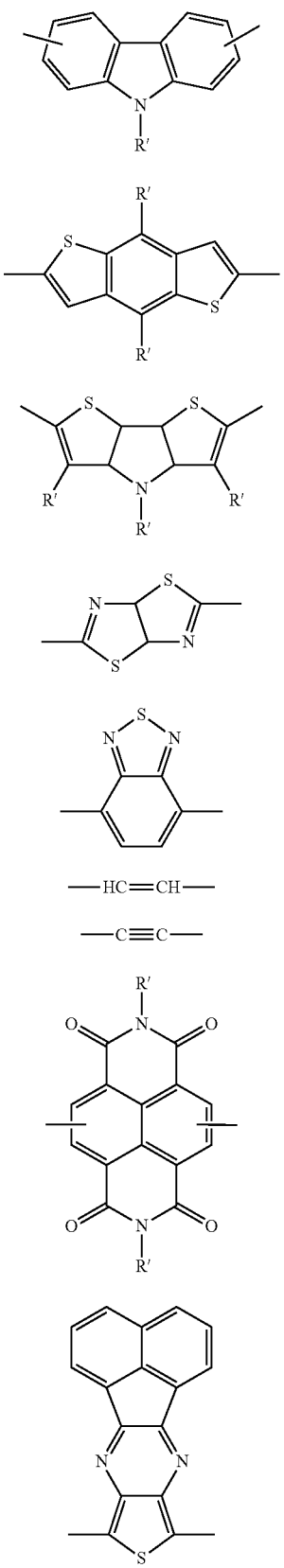

(L-12)
(L-13)
(L-14)
(L-15)
(L-16)
(L-17)
(L-18)
(L-19)
(L-20)

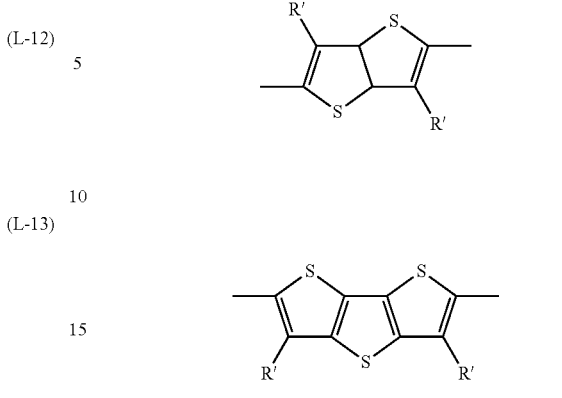

(L-21)
(L-22)

where R' represents, identically or differently in each occurrence, a group selected from hydrogen, optionally substituted alkyl, optionally substituted aryl, optionally substituted heteroaryl, optionally substituted alkoxy, optionally substituted thioalkyl, optionally substituted trialkylsilyl, halogen, cyano, and nitro. When $L^2$ includes two or more occurrences of R', the two or more occurrences of R' may be linked to each other to form a ring with one or more carbon atoms constituting $L^2$, and where, when $L^2$ includes two or more occurrences of R', the two or more occurrences of R' may be linked to each other to form a ring with one or more carbon atoms constituting $L^2$.

The organic semiconductor material to be dissolved in the solvent for organic transistor production may be a compound including a constitutional unit represented by Formula (1-1):

[Chem. 5]

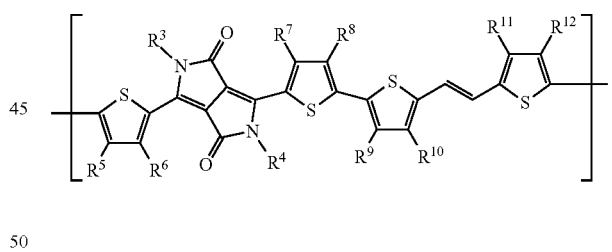

(1-1)

where $R^3$ to $R^{12}$ each represent, identically or differently, a group selected from hydrogen, optionally substituted $C_1$-$C_{24}$ alkyl, optionally substituted aryl, and optionally substituted heteroaryl, where $R^5$ with $R^6$, $R^7$ with $R^8$, $R^9$ with $R^{10}$, and/or $R^{11}$ with $R^{12}$ may independently be linked to form a ring with carbon atoms constituting the thiophene ring.

The present invention also provides a composition for organic transistor production. The composition includes an organic semiconductor material and the solvent for organic transistor production.

The organic semiconductor material in the composition for organic transistor production may be a compound including a constitutional unit represented by Formula (1):

[Chem. 6]

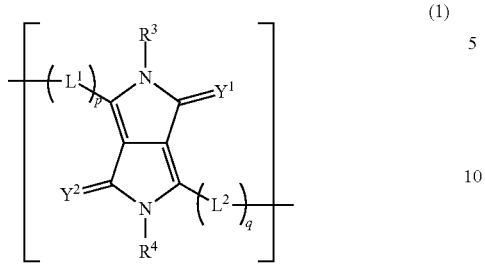

(1)

where $L^1$ and $L^2$ independently represent, identically or differently in each occurrence, a group selected from a group corresponding to an aromatic carbon ring or a heteroaromatic carbon ring, except for removing two hydrogen atoms therefrom, vinylene, ethynylene, and a divalent group including two or more of these groups in combination; $R^3$ and $R^4$ each represent, identically or differently, a group selected from hydrogen, optionally substituted $C_1$-$C_{24}$ alkyl, optionally substituted aryl, and optionally substituted heteroaryl; $Y^1$ and $Y^2$ are each, identically or differently, selected from oxygen and sulfur; p and q each represent, identically or differently, an integer of 0 or more, where the total of p and q is an integer of 1 or more.

In the organic semiconductor material in the composition for organic transistor production, $L^2$ and $L^2$ in Formula (1) may independently be, identically or differently in each occurrence, a group selected from groups represented by Formulae (L-1) to (L-22):

[Chem. 7]

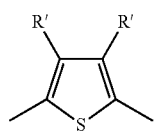 (L-1)

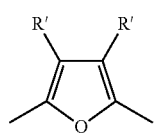 (L-2)

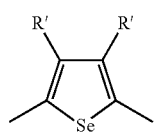 (L-3)

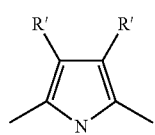 (L-4)

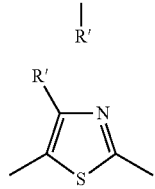 (L-5)

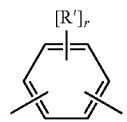 (L-6)

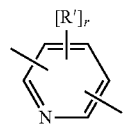 (L-7)

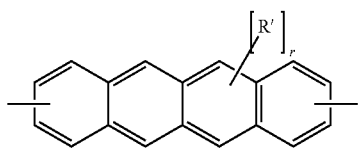 (L-8)

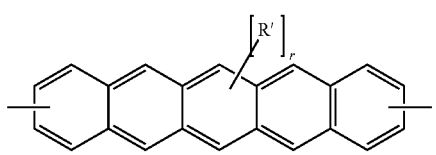 (L-9)

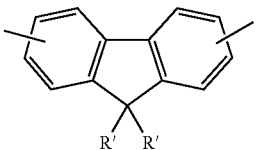 (L-10)

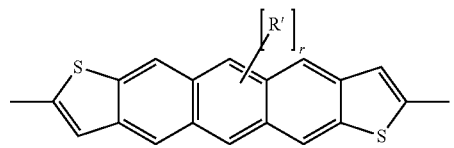 (L-11)

[Chem. 8]

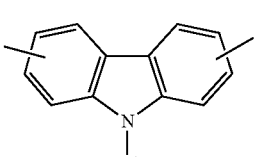 (L-12)

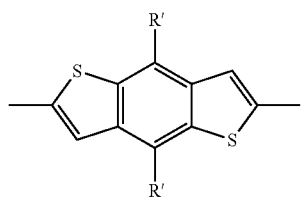 (L-13)

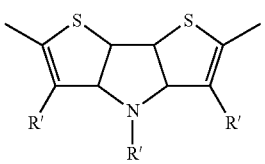 (L-14)

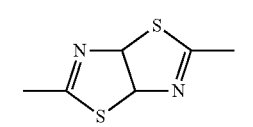 (L-15)

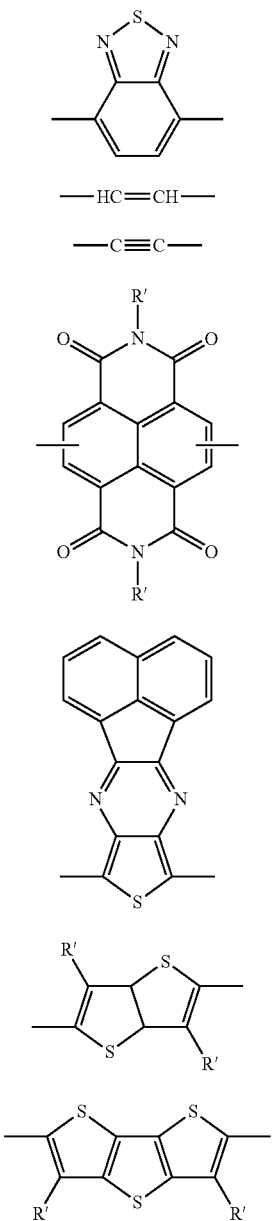

where R' represents, identically or differently in each occurrence, a group selected from hydrogen, optionally substituted alkyl, optionally substituted aryl, optionally substituted heteroaryl, optionally substituted alkoxy, optionally substituted thioalkyl, optionally substituted trialkylsilyl, halogen, cyano, and nitro. When $L^1$ includes two or more occurrences of R', the two or more occurrences of R' may be linked to each other to form a ring with one or more carbon atoms constituting $L^1$. When $L^2$ includes two or more occurrences of R', the two or more occurrences of R' may be linked to each other to form a ring with one or more carbon atoms constituting $L^2$.

The organic semiconductor material in the composition for organic transistor production may be a compound including a constitutional unit represented by Formula (1-1):

[Chem. 9]

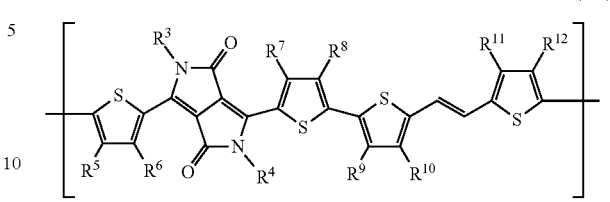

where $R^3$ to $R^{12}$ each represent, identically or differently, a group selected from hydrogen, optionally substituted $C_1$-$C_{24}$ alkyl, optionally substituted aryl, and optionally substituted heteroaryl, where $R^5$ with $R^6$, $R^7$ with $R^8$, $R^9$ with $R^{10}$, and/or $R^{11}$ with $R^{12}$ may independently be linked to form a ring with carbon atoms constituting thiophene ring.

Specifically, the present invention relates to followings.

(1) The present invention relates to a solvent for organic transistor production. The solvent is a solvent for dissolving an organic semiconductor material and includes a solvent A represented by Formula (a).

(2) The solvent A in the solvent according to (1) for organic transistor production may be at least one selected from the group consisting of cyclopentanone, $C_1$-$C_7$ (cyclo)alkylcyclopentanone, cyclohexanone, $C_1$-$C_7$ (cyclo)alkylcyclohexanone, cyclohexyl methyl ether, cyclohexylamine, anisole, 1-methoxy-2-methylbenzene, benzofuran, 2,3-dihydrobenzofuran, dihydromethylbenzofuran, cyclohexyl acetate, dihydroterpinyl acetate, tetrahydrobenzyl acetate, benzyl acetate, tetrahydrofurfuryl acetate, dimethoxybenzene, ethoxybenzene, dipropylene glycol cyclopentyl methyl ether, and N-methylpyrrolidone.

(3) The solvent A in the solvent according to (1) for organic transistor production may be at least one selected from the group consisting of 2-methylcyclopentanone, 2-methylcyclohexanone, cyclohexyl methyl ether, cyclohexylamine, methoxybenzene, 1,2-dimethoxybenzene, 2,3-dihydrobenzofuran, and 2,3-dihydro-3-methylbenzofuran.

(4) The solvent according to any one of (1) to (3) for organic transistor production may contain the solvent A in a content of 50% by weight or more, based on the total amount of the solvent for organic transistor production.

(5) The organic semiconductor material to be dissolved in the solvent according to any one of (1) to (4) for organic transistor production may be the compound including the constitutional unit represented by Formula (1).

(6) In the organic semiconductor material to be dissolved in the solvent according to (5) for organic transistor production, $L^2$ and $L^2$ in Formula (1) may independently be, identically or differently in each occurrence, a group selected from the groups represented by Formulae (L-1) to (L-22).

(7) The organic semiconductor material to be dissolved in the solvent according to any one of (1) to (4) for organic transistor production may be the compound including the constitutional unit represented by Formula (1-1).

(8) The present invention also relates to a composition for organic transistor production. The composition includes an organic semiconductor material and the solvent according to any one of (1) to (7) for organic transistor production.

(9) The organic semiconductor material in the composition according to (8) for organic transistor production may be the compound including the constitutional unit represented by Formula (1).

(10) In the organic semiconductor material in the composition according to (9) for organic transistor production, $L^1$ and $L^2$ in Formula (1) may independently be, identically or differently in each occurrence, a group selected from the groups represented by Formulae (L-1) to (L-22).

(11) The organic semiconductor material in the composition according to (8) for organic transistor production may be the compound including the constitutional unit represented by Formula (1-1).

(12) The organic semiconductor material in the composition according to (8) for organic transistor production may be at least one of a compound including a constitutional unit represented by Formula (1-1a) and a compound including a constitutional unit represented by Formula (1-1b).

(13) The composition according to any one of (8) to (12) for organic transistor production may contain the organic semiconductor material in an amount of 0.01 to 10 parts by weight per 100 parts by weight of the solvent for organic transistor production.

(14) The composition according to any one of (8) to (13) for organic transistor production may contain, as the organic semiconductor material, 0.01 to 10 parts by weight of at least one of the compound including the constitutional unit represented by Formula (1-1a) and the compound including the constitutional unit represented by Formula (1-1b), per 100 parts by weight of the solvent for organic transistor production.

(15) The composition according to any one of (8) to (14) for organic transistor production may contain the solvent for organic transistor production in an amount of 90.00% to 99.99% by weight based on the total amount of the composition for organic transistor production.

Advantageous Effects of Invention

The solvent according to the present invention for organic transistor production has high solubility for organic semiconductor materials even at relatively low temperatures. The solvent thereby enables direct formation of an organic transistor even directly on a plastic substrate or another substrate, where the plastic substrate, although having lower heat resistance, is impact-resistant, lightweight, and flexible, as compared with glass substrates. Thus, the solvent enables the formation of displays and computer devices that are impact-resistant, lightweight, and flexible. The solvent also enables production of an organic transistor easily by a simple procedure via a wet process such as printing process or spin coating process and enables significant cost reduction.

The composition according to the present invention for organic transistor production, when applied onto a substrate, allows the organic semiconductor material to crystallize via self-assembly activity and gives an organic transistor having high crystallinity.

DESCRIPTION OF EMBODIMENTS

Solvent for Organic Transistor Production

The solvent according to the present invention for organic transistor production is a solvent for dissolving an organic semiconductor material and includes a solvent A represented by Formula (a):

[Chem. 10]

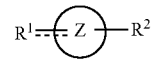

(a)

where Ring Z represents a ring selected from an aromatic carbon ring, a 5- to 7-membered alicyclic carbon ring, and a 5- to 7-membered heterocyclic ring; $R^1$ represents a group selected from oxo ($=$O), thioxy ($=$S), —$OR^a$, —$SR^a$, —$O(C=O)R^a$, —$R^bO(C=O)R^a$, and substituted or unsubstituted amino, where $R^a$ is selected from $C_1$-$C_7$ alkyl, aryl, and a group including two or more of these groups bonded to each other via a single bond or a linkage group, and $R^b$ is selected from $C_1$-$C_7$ alkylene, arylene, and a group including two or more of these groups bonded to each other via a single bond or a linkage group; and $R^2$ represents a group selected from hydrogen, $C_1$-$C_7$ alkyl, aryl, and —$OR^a$, where $R^a$ is as defined above. $R^1$ and $R^2$ may be linked to each other to form a ring with one or more carbon atoms constituting Ring Z.

Solvent A

The solvent A for use in the present invention is a compound that is represented by Formula (a) and contains at least one heteroatom. In Formula (a), Ring Z represents a ring selected from an aromatic carbon ring, a 5- to 7-membered alicyclic carbon ring, and a 5- to 7-membered heterocyclic ring. Non-limiting examples of the ring include $C_6$-$C_{14}$ aromatic carbon rings such as benzene ring; 5- to 7-membered alicyclic carbon rings such as cyclopentane, cyclohexane, and cycloheptane rings, of which 5- to 7-membered alkane rings are typified; and 5- to 7-membered heterocyclic rings such as pyrrolidine, oxolane, and thiolane rings.

In Formula (a), $R^1$ represents a group selected from oxo ($=$O), thioxy ($=$S), —$OR^a$, —$SR^a$, —$O(C=O)R^a$, —$R^bO(C=O)R^a$, and substituted or unsubstituted amino, where $R^a$ is selected from $C_1$-$C_7$ alkyl, aryl, and a group including two or more of these groups bonded to each other via a single bond or a linkage group, and $R^b$ is selected from $C_1$-$C_7$ alkylene, arylene, and a group including two or more of these groups bonded to each other via a single bond or a linkage group; and $R^2$ represents a group selected from hydrogen, $C_1$-$C_7$ alkyl, aryl, and —$OR^a$, where $R^a$ is as defined above.

Non-limiting examples of the $C_1$-$C_7$ alkyl include straight or branched chain alkyl such as methyl, ethyl, propyl, butyl, pentyl, hexyl, and heptyl; and $C_3$-$C_7$ cycloalkyl such as cyclopentyl.

Non-limiting examples of the $C_1$-$C_7$ alkylene include straight or branched chain alkylene such as methylene, methylmethylene, dimethylmethylene, ethylene, propylene, and trimethylene.

Non-limiting examples of the aryl include $C_6$-$C_{14}$ aryl such as phenyl.

Examples of the arylene include, but are not limited to, $C_6$-$C_{14}$ arylene such as phenylene.

Non-limiting examples of the linkage group include alkylene, carbonyl (—CO—), ether bond (—O—), ester bond (—COO—), amide bond (—CONH—), carbonate bond (—OCOO—), and groups each including two or more of them linked to each other. The alkylene preferably contains 1 to 18 carbon atoms, and is exemplified by, but not limited to, straight or branched chain alkylene such as methylene, methylmethylene, dimethylmethylene, ethylene, propylene, and trimethylene; and divalent alicyclic hydrocarbon groups such as 1,2-cyclopentylene, 1,3-cyclopentylene, cyclopentylidene, 1,2-cyclohexylene, 1,3-cyclohexylene, 1,4-cyclohexylene, and cyclohexylidene, of which cycloalkylene is typified.

Non-limiting examples of the substituted or unsubstituted amino include amino; and mono- or di-($C_1$-$C_3$ alkyl)-amino such as methylamino, ethylamino, isopropylamino, dimethylamino, and diethylamino.

$R^1$ and $R^2$ may be linked to each other to form a ring with one or more carbon atoms constituting Ring Z. Examples of the ring include, but are not limited to, cyclopentane, cyclohexane, cycloheptane, benzene, methylbenzene, thiophene, methylthiophene, furan, methylfuran, dihydrofuran, and methyldihydrofuran.

The solvent A represented by Formula (a) may have a weight-average molecular weight of typically about 350 or less, preferably 70 to 250, and particularly preferably 80 to 200.

Non-limiting examples of the solvent A for use in the present invention include cyclopentanone, $C_1$-$C_7$ (cyclo)alkylcyclopentanones (such as 2-methylcyclopentanone, 2-ethylcyclopentanone, 2-propylcyclopentanone, 2-butylcyclopentanone, 2-pentylcyclopentanone, 2-cyclopentylcyclopentanone, 2-hexylcyclopentanone, and 2-heptylcyclopentanone), cyclohexanone, $C_1$-$C_7$ (cyclo)alkylcyclohexanones (such as 2-methylcyclohexanone, 2-ethylcyclohexanone, 2-propylcyclohexanone, 2-butylcyclohexanone, 2-pentylcyclohexanone, 2-hexylcyclohexanone, 2-heptylcyclohexanone, and 4-pentylcyclohexanone), cyclohexyl methyl ether, cyclohexylamine, anisole (i.e., methoxybenzene), 1-methoxy-2-methylbenzene, benzofuran, 2,3-dihydrobenzofuran, dihydromethylbenzofurans (such as 2,3-dihydro-3-methylbenzofuran), cyclohexyl acetate, dihydroterpinyl acetate, tetrahydrobenzyl acetate, benzyl acetate, tetrahydrofurfuryl acetate, dimethoxybenzenes (such as 1,2-dimethoxybenzene), ethoxybenzene, dipropylene glycol cyclopentyl methyl ether, and N-methylpyrrolidone. The solvent may include each of different solvents A alone or in combination. As used herein the term "(cyclo)alkyl" refers to an alkyl or a cycloalkyl.

Assume that the compound including the constitutional unit represented by Formula (1-1) (in particular, the compound including the constitutional unit represented by Formula (1-1a)) as described below is to be dissolved as the organic semiconductor material. In particular in this case, the solvent A is preferably at least one selected from the group consisting of 2-methylcyclopentanone, 2-methylcyclohexanone, cyclohexyl methyl ether, cyclohexylamine, anisole (i.e., methoxybenzene), 1,2-dimethoxybenzene, 2,3-dihydrobenzofuran, and 2,3-dihydro-3-methylbenzofuran, because these have excellent solubility for the organic semiconductor material.

The solvent for organic transistor production may contain the solvent A in a content of preferably 50% by weight or more (e.g., 50% to 100% by weight), and particularly preferably 70% by weight or more (e.g., 70% to 100% by weight), based on the total amount (100% by weight) of the solvent for organic transistor production. When the solvent for organic transistor production contains two or more different solvents A, the term "content" refers to the total content of them. The solvent for organic transistor production, if containing the solvent A in a content less than the range, tends to have lower solubility for the organic semiconductor material.

Solvent B

The solvent according to the present invention for organic transistor production may contain a solvent B in combination with the solvent A. The solvent B is a solvent that is generally used for electron material uses and is compatible with (miscible with) the solvent A.

Non-limiting examples of the solvent B include (mono-, di-, or tri-)alkylene glycol monoalkyl ethers, (mono- or di-)alkylene glycol dialkyl ethers, (mono- or di-)alkylene glycol alkyl ether acetates, (mono- or di-)alkylene glycol diacetates, alkyl acetates, $C_3$-$C_6$ alcohols, $C_3$-$C_6$ alkanediols, $C_3$-$C_6$ alkanediol monoalkyl ethers, $C_3$-$C_6$ alkanediol alkyl ether acetates, $C_3$-$C_6$ alkanediol diacetates, glycerol triacetate, hydroxycarboxylic acid esters, hydroxycarboxylic acid diesters, alkoxycarboxylic acid esters, cyclic ketones, lactones, cyclic ethers, amides, pyridines, aromatic acetates, and amines. The solvent for organic transistor production may contain each of different solvents B alone or in combination.

Non-limiting examples of the (mono-, di-, or tri-)alkylene glycol monoalkyl ethers include ethylene glycol monomethyl ether, ethylene glycol monoethyl ether, ethylene glycol n-propyl ether, ethylene glycol n-butyl ether, diethylene glycol monomethyl ether, diethylene glycol monoethyl ether, diethylene glycol n-propyl ether, diethylene glycol n-butyl ether, propylene glycol monomethyl ether, propylene glycol monoethyl ether, propylene glycol n-propyl ether, propylene glycol n-butyl ether, dipropylene glycol monomethyl ether, dipropylene glycol monoethyl ether, dipropylene glycol n-propyl ether, dipropylene glycol n-butyl ether, tripropylene glycol monomethyl ether, and tripropylene glycol n-butyl ether.

Non-limiting examples of the (mono- or di-)alkylene glycol dialkyl ethers include ethylene glycol dimethyl ether, ethylene glycol diethyl ether, diethylene glycol dimethyl ether, diethylene glycol diethyl ether, diethylene glycol dipropyl ether, diethylene glycol dibutyl ether, propylene glycol dimethyl ether, propylene glycol diethyl ether, dipropylene glycol dimethyl ether, dipropylene glycol diethyl ether, propylene glycol methyl ethyl ether, propylene glycol methyl n-propyl ether, propylene glycol methyl n-butyl ether, dipropylene glycol methyl ethyl ether, dipropylene glycol methyl n-propyl ether, and dipropylene glycol methyl n-butyl ether.

Non-limiting examples of the (mono- or di-)alkylene glycol alkyl ether acetates include ethylene glycol monomethyl ether acetate, ethylene glycol monoethyl ether acetate, ethylene glycol monopropyl ether acetate, ethylene glycol monobutyl ether acetate, diethylene glycol monomethyl ether acetate, diethylene glycol monoethyl ether acetate, diethylene glycol monopropyl ether acetate, diethylene glycol monobutyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, dipropylene glycol monopropyl ether acetate, and dipropylene glycol monobutyl ether acetate.

Non-limiting examples of the (mono- or di-)alkylene glycol diacetates include ethylene glycol diacetate, diethylene glycol diacetate, propylene glycol diacetate, and dipropylene glycol diacetate.

Non-limiting examples of the alkyl acetates include methyl acetate, ethyl acetate, n-propyl acetate, isopropyl acetate, and butyl acetate.

Examples of the $C_3$-$C_6$ alcohols include, but are not limited to, n-propyl alcohol, isopropyl alcohol, n-butyl alcohol, sec-butyl alcohol, tert-butyl alcohol, n-pentyl alcohol, n-hexyl alcohol, and 2-hexyl alcohol.

Examples of the $C_3$-$C_6$ alkanediols include, but are not limited to, 1,3-butylene glycol, 1,4-butanediol, and 1,6-hexanediol.

A non-limiting example of the $C_3$-$C_6$ alkanediol monoalkyl ethers is 3-methoxybutanol.

A non-limiting example of the $C_3$-$C_6$ alkanediol alkyl ether acetates is 3-methoxybutanol acetate.

Non-limiting examples of the $C_3$-$C_6$ alkanediol diacetates include 1,3-butylene glycol diacetate, 1,4-butanediol diacetate, and 1,6-hexanediol diacetate.

Non-limiting examples of the hydroxycarboxylic acid esters include methyl lactate and ethyl lactate.

Non-limiting examples of the hydroxycarboxylic acid diesters include methyl lactate acetate and ethyl lactate acetate.

Non-limiting examples of the alkoxycarboxylic acid esters include methoxymethyl propionate and ethoxyethyl propionate.

A non-limiting example of the cyclic ketones is 4-ketoisophorone.

Non-limiting examples of the lactones include β-butyrolactone, γ-butyrolactone, ε-caprolactone, δ-valerolactone, γ-valerolactone, and α-acetyl-γ-butyrolactone.

Non-limiting examples of the cyclic ethers include tetrahydrofuran and tetrahydrofurfuryl alcohol.

A non-limiting example of the amides is dimethylformamide.

Non-limiting examples of the pyridines include pyridine and methylpyridine.

A non-limiting example of the aromatic acetates is phenyl acetate.

Non-limiting examples of the amines include diethylamine and triethylamine.

The combination use of the solvent A and the solvent B in the present invention can give a composition for organic transistor production that contains the organic semiconductor material in a high concentration and has properties such as coatability, drying behavior, safety, dispersibility, and solubility at excellent levels.

For still better coatability, it is effective to use the solvent A in combination with at least one solvent selected from the group consisting of the (mono-, di-, or tri-)alkylene glycol monoalkyl ethers, the (mono- or di-)alkylene glycol dialkyl ethers, the (mono- or di-)alkylene glycol alkyl ether acetates, the (mono- or di-)alkylene glycol diacetates, and the alkoxycarboxylic acid esters.

For still better pigment dispersibility, it is effective to use the solvent A in combination with at least one solvent selected from the group consisting of mono-$C_3$-$C_6$ alkylene glycol alkyl ether acetates (such as propylene glycol monomethyl ether acetate) and $C_3$-$C_6$ alkanediol alkyl ether acetates.

For still better dye solubility, it is effective to use the solvent A in combination with at least one solvent selected from the group consisting of mono-$C_3$-$C_6$ alkylene glycol monoalkyl ethers (such as propylene glycol monomethyl ether), mono-$C_3$-$C_6$ alkylene glycol alkyl ether acetates (such as propylene glycol monomethyl ether acetate), $C_3$-$C_6$ alkanediol monoalkyl ethers, $C_3$-$C_6$ alkanediol alkyl ether acetates, hydroxycarboxylic acid esters, hydroxycarboxylic acid diesters, $C_3$-$C_6$ alcohols, and $C_3$-$C_6$ alkanediols.

For still better solubility for epoxy resins and acrylic resins, it is effective to use the solvent A in combination with at least one solvent selected from the group consisting of (mono-, di-, or tri-)alkylene glycol monoalkyl ethers, (mono- or di-)alkylene glycol dialkyl ethers, (mono- or di-)alkylene glycol alkyl ether acetates, (mono- or di-)alkylene glycol diacetates, cyclic ketones, lactones, cyclic ethers, amides, pyridines, aromatic acetates, and amines.

For still better drying behavior, it is effective to use the solvent A in combination with at least one solvent selected from the group consisting of (mono- or di-)$C_3$-$C_6$ alkylene glycol $C_1$-$C_2$ alkyl $C_3$-$C_4$ alkyl ethers (such as propylene glycol methyl n-propyl ether, propylene glycol methyl n-butyl ether, dipropylene glycol methyl n-propyl ether, and dipropylene glycol methyl n-butyl ether); and alkyl acetates.

When the solvent A and the solvent B are used in combination, the ratio (weight ratio) of the solvent A to the solvent B is typically from 50:50 to 95:5, and preferably from 70:30 to 95:5. The solvent for organic transistor production, if containing the solvent B in an excessively large proportion relative to the solvent A, tends to have lower solubility for the organic semiconductor material. When two or more different solvents are used in combination as the solvent A, the proportion of the solvent A refers to the total amount of the two or more solvents. This is also true for the solvent B.

The solvent according to the present invention for organic transistor production, as containing the solvent A, has high solubility for organic semiconductor materials even at relatively low temperatures. For example, the compound including the constitutional unit represented by Formula (1) has a solubility at 100° C. of typically 0.02 part by weight or more, preferably 0.03 part by weight or more, and particularly preferably 0.04 part by weight or more, in 100 parts by weight of the solvent for organic transistor production. The upper limit of the solubility is typically 5 parts by weight, preferably 3 parts by weight, and particularly preferably 2 parts by weight.

Organic Semiconductor Material

The solvent according to the present invention for organic transistor production is a solvent for dissolving an organic semiconductor material. The organic semiconductor material is not limited, but is herein preferably a compound including a constitutional unit represented by Formula (1) and contains an optionally substituted diketopyrrolopyrrole group. The compound is preferred because the constitutional unit acts as an acceptor group and can have an orderly arrayed/oriented structure with respect to a donor group, where the orderly arrayed/oriented structure is given by strong π-stacking due to the intermolecular electronic interaction between the donor and the acceptor. The repetition number of the constitutional unit represented by Formula (1) is typically about 2 to about 5000. Formula (1) is expressed as follows:

[Chem. 11]

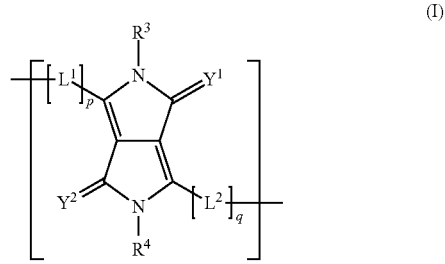

where $L^1$ and $L^2$ independently represent, identically or differently in each occurrence, a group selected from a group corresponding to an aromatic carbon ring or a heteroaromatic carbon ring, except for removing two hydrogen atoms therefrom, vinylene, ethynylene, and a divalent group including two or more of these groups in combination; $R^3$ and $R^4$ each represent, identically or differently, a group selected from hydrogen, optionally substituted $C_1$-$C_{24}$ alkyl, optionally substituted aryl, and optionally substituted heteroaryl; $Y^1$ and $Y^2$ are each, identically or differently, selected from oxygen and sulfur; and p and q each represent, identically or differently, an integer of 0 or more, where the total of p and q is an integer of 1 or more. In the formula, "p" occurrences of $L^1$ may be identical or different, and "q" occurrences of $L^2$ may be identical or different.

In Formula (1), $R^3$ and $R^4$ each represent, identically or differently, a group selected from hydrogen, optionally substituted $C_1$-$C_{24}$ alkyl, optionally substituted aryl, and optionally substituted heteroaryl. Non-limiting examples of the $C_1$-$C_{24}$ alkyl include $C_1$-$C_{24}$ straight or branched chain alkyl such as methyl, ethyl, propyl, butyl, pentyl, hexyl, heptyl, decyl, dodecyl, octadecyl, and icosyl. Non-limiting examples of the aryl include $C_6$-$C_{14}$ aryl such as phenyl. Non-limiting examples of the heteroaryl include 2-furyl, 3-furyl, 2-thienyl, 3-thienyl, 2-pyrrolyl, 3-pyrrolyl, 2-oxazolyl, 2-thiazolyl, 2-imidazolyl, 2-pyridyl, 3-pyridyl, 4-pyridyl, 2-benzofuryl, 2-benzothienyl, and 2-thienothienyl. Non-limiting examples of substituents which the groups may have include hydroxy and carboxy.

$L^1$ and $L^2$ independently represent, identically or differently in each occurrence, a group selected from a group corresponding to an aromatic carbon ring or a heteroaromatic carbon ring, except for removing two hydrogen atoms therefrom, vinylene, ethynylene, and a divalent group including two or more of these groups in combination.

Non-limiting examples of the aromatic carbon ring include benzene, naphthalene, anthracene, phenanthrene, tetracene, chrysene, pyrene, triphenylene, and pentacene.

Non-limiting examples of the heteroaromatic carbon ring include pyrrole, pyridine, furan, thiophene, selenophene, imidazole, pyrazole, oxazole, 1,3-thiazole, imidazoline, pyrazine, morpholine, thiazine, and 1,3,4-thiadiazole.

Among them, $L^2$ and $L^2$ herein are independently preferably a group selected from groups represented by Formulae (L-1) to (L-22):

[Chem. 12]

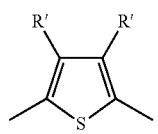
(L-1)

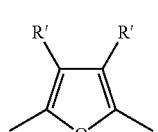
(L-2)

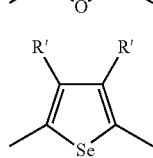
(L-3)

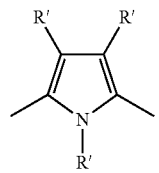
(L-4)

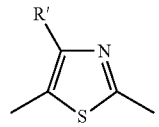
(L-5)

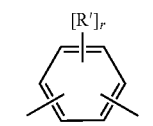
(L-6)

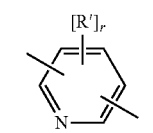
(L-7)

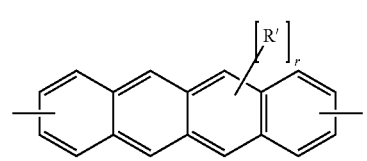
(L-8)

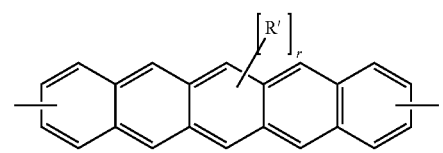
(L-9)

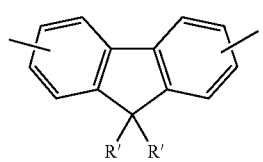
(L-10)

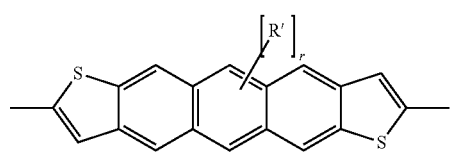
(L-11)

[Chem. 13]

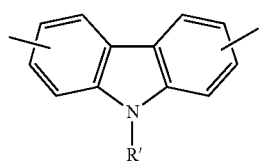
(L-12)

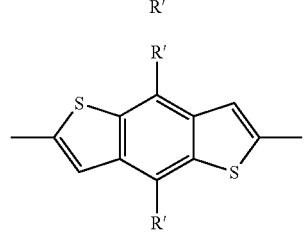
(L-13)

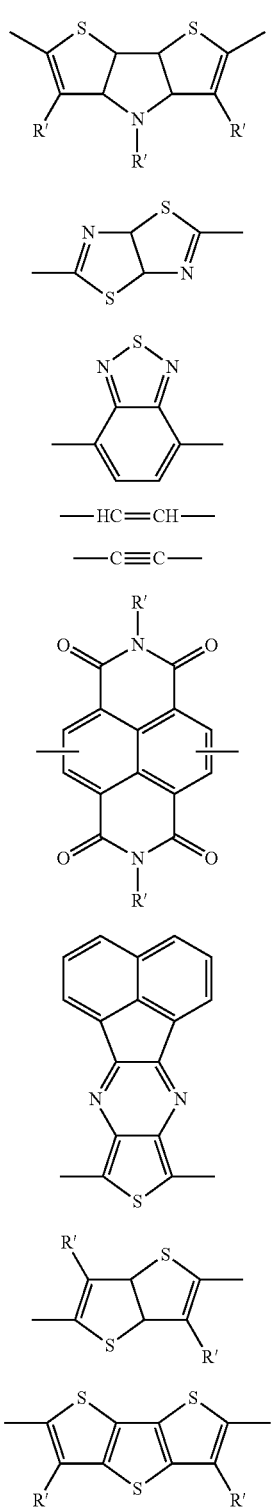

(L-14)
(L-15)
(L-16)
(L-17) —HC=CH—
(L-18) —C≡C—
(L-19)
(L-20)
(L-21)
(L-22)

In the formulae, R' represents, identically or differently in each occurrence, a group selected from hydrogen, optionally substituted alkyl, optionally substituted aryl, optionally substituted heteroaryl, optionally substituted alkoxy, optionally substituted thioalkyl, optionally substituted trialkylsilyl, halogen, cyano, and nitro. When a group represented by any of the formulae contains two or more occurrences of R', the two or more occurrences of R' may be linked to each other to form a ring with one or more carbon atoms constituting the group.

Non-limiting examples of the alkyl include $C_1$-$C_{24}$ straight or branched chain alkyl such as methyl, ethyl, propyl, butyl, pentyl, and hexyl.

Non-limiting examples of the aryl include $C_6$-$C_{14}$ aryl such as phenyl.

Non-limiting examples of the heteroaryl include 2-furyl, 3-furyl, 2-thienyl, 3-thienyl, 2-pyrrolyl, 3-pyrrolyl, 2-oxazolyl, 2-thiazolyl, 2-imidazolyl, 2-pyridyl, 3-pyridyl, 4-pyridyl, 2-benzofuryl, 2-benzothienyl, and 2-thienothienyl.

Non-limiting examples of the alkoxy include $C_1$-$C_{24}$ alkoxy such as methoxy, ethoxy, propoxy, isopropoxy, butoxy, isobutoxy, t-butoxy, pentyloxy, and hexyloxy.

Non-limiting examples of the thioalkyl include thio-$C_1$-$C_{24}$ alkyl such as thiomethyl, thioethyl, thiopropyl, thioisopropyl, thiobutyl, thioisobutyl, thio-sec-butyl, thio-tert-butyl, thiopentyl, and thiohexyl.

Non-limiting examples of the trialkylsilyl include tri-(($C_1$-$C_{24}$) alkyl and/or aryl)silyl such as trimethylsilyl, tert-butyldimethylsilyl, tribenzylsilyl, and triphenylsilyl.

Non-limiting examples of the halogen include fluorine, chlorine, bromine, and iodine.

Non-limiting examples of substituents which the groups may have include optionally protected hydroxy, optionally protected hydroxymethyl, optionally protected amino, optionally protected carboxy, optionally protected sulfo, halogen, oxo, cyano, nitro, heterocyclic groups, hydrocarbon groups, and haloalkyl. Such protecting groups may be selected from protecting groups commonly used in the field of organic syntheses.

The two or more occurrences of R', when present, may be linked to each other to form a ring with one or more carbon atoms constituting $L^1$ or $L^2$. Non-limiting examples of the ring include cyclopentane, cyclohexane, cycloheptane, benzene, methylbenzene, thiophene, methylthiophene, furan, methylfuran, dihydrofuran, and methyldihydrofuran.

In the formulae, r represents, for example, an integer of 1 to 3.

Of the compounds including the constitutional unit represented by Formula (1), preferred as the organic semiconductor material are compounds containing an optionally substituted diketopyrrolopyrrole group in combination with vinylene and a group corresponding to thiophene, except for removing two hydrogen atoms from the thiophene. These compounds are preferred because they have an orderly arrayed/oriented structure due to strong π-stacking via the donor-acceptor intermolecular electronic interaction. Non-limiting example of the compounds just mentioned above include compounds including a constitutional unit represented by Formula (1-1):

[Chem. 14]

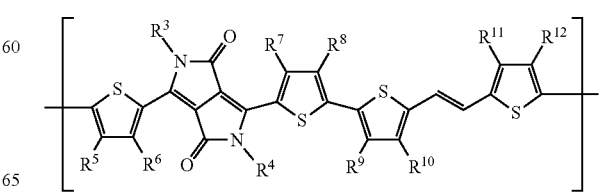

(1-1)

In the formula, $R^3$ to $R^{12}$ each represent, identically or differently, a group selected from hydrogen, optionally substituted $C_1$-$C_{24}$ alkyl, optionally substituted aryl, and optionally substituted heteroaryl, where $R^5$ with $R^6$, $R^7$ with $R^8$, $R^9$ with $R^{10}$, and/or $R^{11}$ with $R^{12}$ may independently be linked to form a ring with carbon atoms constituting the thiophene ring. In $R^3$ to $R^{12}$, examples of the optionally substituted $C_1$-$C_{24}$ alkyl, the optionally substituted aryl, the optionally substituted heteroaryl, and the ring which may be formed with carbon atoms constituting the thiophene ring are as in R'.

Of the compounds including a constitutional unit represented by Formula (1-1), those in which $R^5$ to $R^{12}$ are hydrogen are preferred as the organic semiconductor material for use in the present invention. In particular, a compound including at least one of a constitutional unit represented by Formula (1-1a) and a constitutional unit represented by Formula (1-1b) is preferably used to give an organic transistor having high stacking tendency.

[Chem. 15]

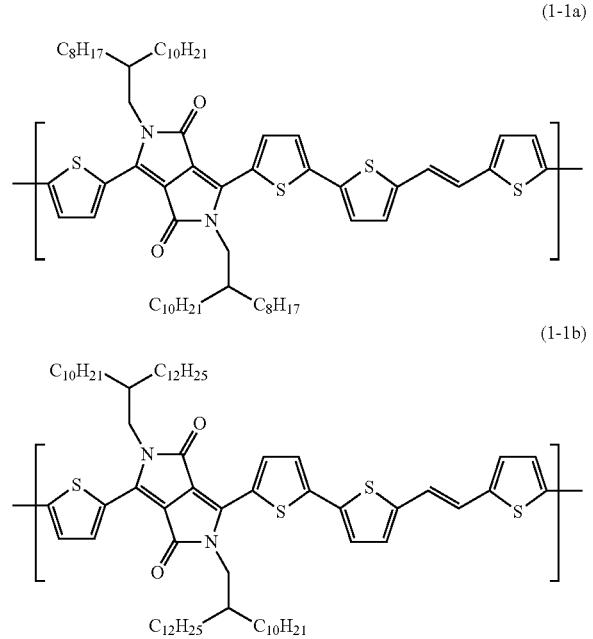

(1-1a)

(1-1b)

The compound including the constitutional unit represented by Formula (1) may have a weight-average molecular weight of typically about 5000000 or less, preferably 1000 to 1000000, and particularly preferably 5000 to 500000.

Composition for Organic Transistor Production

The composition according to the present invention for organic transistor production includes the organic semiconductor material and the solvent for organic transistor production.

The composition according to the present invention for organic transistor production may be prepared typically by mixing the organic semiconductor material with the solvent for organic transistor production and heating them at a temperature of about 70° C. to 150° C. in the air for about 0.1 to about 2 hours.

Assume that the compound including the constitutional unit represented by Formula (1) is used as the organic semiconductor material. Typically in this case, the composition according to the present invention for organic transistor production may contain the organic semiconductor material in a content of typically 0.02 part by weight or more, preferably 0.03 part by weight or more, and particularly preferably 0.04 part by weight or more, per 100 parts by weight of the solvent for organic transistor production. The upper limit of the content is typically 5 parts by weight, preferably 3 parts by weight, and particularly preferably 2 parts by weight.

Assume that the compound including at least one of the constitutional unit represented by Formula (1-1a) and the constitutional unit represented by Formula (1-1b) is used as the organic semiconductor material. In this case, the content of the compound is typically 0.01 part by weight or more, preferably 0.05 part by weight or more, more preferably 0.1 part by weight or more, and particularly preferably 0.2 part by weight or more, per 100 parts by weight of the solvent for organic transistor production. When two or more different compounds are used in combination as the organic semiconductor material, the term "content" refers to the total content of the two or more compounds. The upper limit of the content is typically 10 parts by weight, preferably 7 parts by weight, and particularly preferably 5 parts by weight.

The composition according to the present invention for organic transistor production may contain the solvent for organic transistor production in a content of typically 99.99% by weight or less. The lower limit of the content is typically 90.00% by weight, preferably 93.00% by weight, and particularly preferably 95.00% by weight; and the upper limit of the content is preferably 99.95% by weight, and particularly preferably 99.90% by weight.

The content of the solvent for organic transistor production in the composition according to the present invention for organic transistor production is typically preferably 10 times (by weight) or more, more preferably 13 times (by weight) or more, and particularly preferably 20 times (by weight) or more the weight of the organic semiconductor material (e.g., the compound including the constitutional unit represented by Formula (1)). This is preferred for accelerating crystallization of the organic semiconductor material via self-assembly activity. The upper limit of the content is typically 10000 times (by weight), preferably 2000 times (by weight), more preferably 1000 times (by weight), and particularly preferably 500 times (by weight).

In addition to the organic semiconductor material and the solvent for organic transistor production, the composition according to the present invention for organic transistor production may include one or more components for use in common compositions for organic transistor production as needed and as appropriate. Non-limiting examples of the components include epoxy resins, acrylic resins, cellulose resins, and butyral resins.

The composition according to the present invention for organic transistor production dissolves the organic semiconductor material in a high concentration even at relatively low temperatures. This enables the formation of an organic transistor even directly on a plastic substrate, where the plastic substrate, although having lower heat resistance, is impact-resistant, lightweight, and flexible as compared with glass substrates. Thus, the composition enables the formation of displays and computer devices that are impact-resistant, lightweight, and flexible. The composition according to the present invention for organic transistor production contains the solvent according to the present invention for organic transistor production and, when applied onto a substrate, allows the organic semiconductor material to crystallize via self-assembly activity and gives an organic transistor having high crystallinity. In addition, the composition enables the formation of an organic transistor easily by a simple procedure via a wet process such as printing process or spin coating process and contributes to significant cost reduction.

EXAMPLES

The present invention will be illustrated in further detail with reference to several examples below. It should be noted, however, that the examples are by no means intended to limit the scope of the present invention.

Example 1

Compositions for organic transistor production having organic semiconductor material concentrations of 0.05% to 0.40% by weight were prepared. The compositions were prepared at an ambient temperature of 20° C. using a compound including a constitutional unit represented by Formula (1-1a) (trade name PDVT-8, supplied by 1-Material, Chemscitech Inc.) as an organic semiconductor material and 2,3-dihydrobenzofuran (DHBF) as a solvent for organic transistor production.

The prepared compositions for organic transistor production were heated at 120° C. in a nitrogen atmosphere under light-blocking conditions for about 2 hours, and whether the organic semiconductor material was dissolved was visually checked. For the solubility, a sample in which no insoluble mater was visually observed was evaluated as "good: dissolved"; and a sample in which insoluble matter was visually observed was evaluated as "poor: undissolved". Hereinafter the same.

Of the compositions for organic transistor production, those that underwent full dissolution were left stand at 20° C. in a nitrogen atmosphere under light-blocking conditions, and the time elapsed before precipitates appeared was measured.

Examples 2 to 7 and Comparative Example 1

Compositions for organic transistor production were prepared, and the solubility of the organic semiconductor material was evaluated by a procedure similar to that in Example 1, except for using solvents given in Table 1 instead of 2,3-dihydrobenzofuran (DHBF).

MANON: 2-methylcyclohexanone (supplied by Wako Pure Chemical Industries, Ltd., molecular weight: 112.17)

MOB: methoxybenzene (supplied by Tokyo Chemical Industry Co., Ltd., molecular weight: 108.14)

DHMDF: 2,3-dihydro-3-methylbenzofuran (supplied by Tokyo Chemical Industry Co., Ltd., molecular weight: 134.18)

DMOB: 1,2-dimethoxybenzene (supplied by Tokyo Chemical Industry Co., Ltd., molecular weight: 138.16)

CHA: cyclohexylamine (supplied by Wako Pure Chemical Industries, Ltd., molecular weight: 99.17)

Example 8 and Comparative Example 2

Compositions for organic transistor production having an organic semiconductor material concentration of 0.10% by weight were prepared. The compositions were prepared at an ambient temperature of 20° C. using a compound including a constitutional unit represented by Formula (1-1b) (trade name PDVT-10, supplied by 1-Material, Chemscitech Inc.) as an organic semiconductor material, and solvents given in Table 2. The prepared compositions for organic transistor production were heated at 120° C. in a nitrogen atmosphere under light-blocking conditions for about 2 hours, and whether the organic semiconductor material was dissolved was visually checked.

Of the compositions for organic transistor production, those underwent full dissolution were left stand at 20° C. in a nitrogen atmosphere under light-blocking conditions, and the time elapsed before precipitates appeared was measured.

TABLE 2

| | Solvent | Solubility of PDVT-10 0.10% | Time elapsed before precipitation (hour) 0.10% |
|---|---|---|---|
| Comparative Example 2 | O-DCB | Good | 0.5 |
| Example 8 | DHBF | Good | >48 |

O-DCB: 1,2-dichlorobenzene (supplied by Tokyo Chemical Industry Co., Ltd.)

DHBF: 2,3-dihydrobenzofuran (supplied by Tokyo Chemical Industry Co., Ltd., molecular weight: 120.15)

TABLE 1

| | | Solubility of PDVT-8 | | | | | Time elapsed before precipitation (hour) | | | | |
|---|---|---|---|---|---|---|---|---|---|---|---|
| | Solvent | 0.05% | 0.10% | 0.15% | 0.35% | 0.40% | 0.05% | 0.10% | 0.15% | 0.35% | 0.40% |
| Comparative Example 1 | O-DCB | Good | Good | Good | Good | Good | — | — | — | 1.5 | 1.5 |
| Example 1 | DHBF | Good | Good | Good | Good | Poor | — | — | — | >48 | — |
| Example 2 | CHXME | Good | Good | Good | Poor | Poor | — | 1.5 | 0.5 | — | — |
| Example 3 | MANON | Good | Good | Poor | Poor | Poor | — | >48 | — | — | — |
| Example 4 | MOB | Good | Good | Poor | Poor | Poor | 1.5 | 0.5 | — | — | — |
| Example 5 | DHMDF | Good | Poor | Poor | Poor | Poor | 12 | — | — | — | — |
| Example 6 | DMOB | Good | Poor | Poor | Poor | Poor | 12 | — | — | — | — |
| Example 7 | CHA | Good | Poor | Poor | Poor | Poor | 3 | — | — | — | — |

O-DCB: 1,2-dichlorobenzene (supplied by Tokyo Chemical Industry Co., Ltd.)

DHBF: 2,3-dihydrobenzofuran (supplied by Tokyo Chemical Industry Co., Ltd., molecular weight: 120.15)

CHXME: cyclohexyl methyl ether (supplied by Wako Pure Chemical Industries, Ltd., molecular weight: 114.19)

INDUSTRIAL APPLICABILITY

The solvent according to the present invention for organic transistor production has high solubility for organic semiconductor materials even at relatively low temperatures. This enables formation of an organic transistor even directly on a plastic substrate or another substrate, where the plastic substrate, although having lower heat resistance, is impact-resistant, lightweight, and flexible as compared with glass substrates. Thus, the solvent enables the formation of displays and computer devices that are impact-resistant, lightweight, and flexible. The solvent also enables the production of the organic transistor easily by a simple procedure via a wet process such as printing process or spin coating process and enables significant cost reduction.

The composition according to the present invention for organic transistor production, when applied onto a substrate, allows the organic semiconductor material to crystallize via self-assembly activity and gives an organic transistor having high crystallinity.

The invention claimed is:

1. A composition for organic transistor production, the composition comprising:
an organic semiconductor material comprising a compound including a constitutional unit represented by Formula (1-1b):

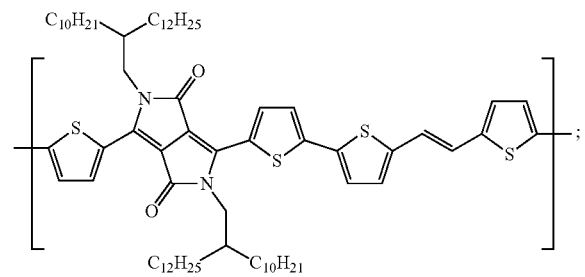

(1-1b)

and a solvent,
the solvent being used for dissolving the organic semiconductor material, the solvent comprising a solvent A, wherein the solvent A comprises at least one selected from the group consisting of 2-methylcyclopentanone, 2-methylcyclohexanone, cyclohexyl methyl ether, cyclohexylamine, 2,3-dihydrobenzofuran, and 2,3-dihydro-3-methylbenzofuran.

2. A composition for organic transistor production, the composition comprising:
an organic semiconductor material comprising a compound including a constitutional unit represented by Formula (1-1a):

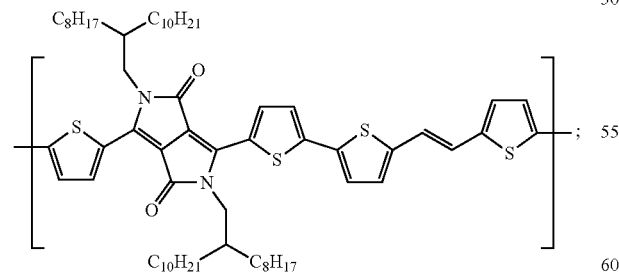

(1-1a)

and a solvent,
the solvent being used for dissolving the organic semiconductor material, the solvent comprising a solvent A', wherein the solvent A' comprises at least one selected from the group consisting of 2-methylcyclopentanone, 2-methylcyclohexanone, cyclohexyl methyl ether, and 2,3-dihydrobenzofuran.

3. A method for producing a composition for organic transistor production comprising dissolving an organic semiconductor material comprising a compound including a constitutional unit represented by Formula (1-1b):

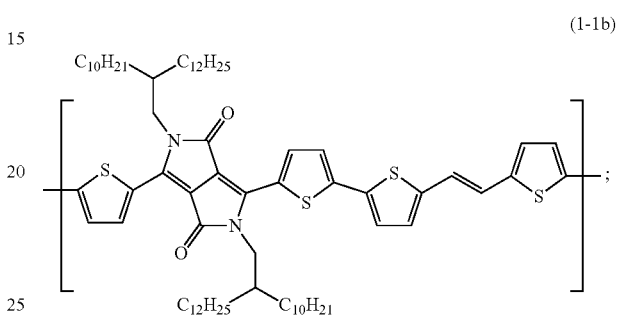

(1-1b)

with a solvent A comprising at least one selected from the group consisting of 2-methylcyclopentanone, 2-methylcyclohexanone, cyclohexyl methyl ether, cyclohexylamine, 2,3-dihydrobenzofuran, and 2,3-dihydro-3-methylbenzofuran.

4. A method for producing a composition for organic transistor production comprising dissolving an organic semiconductor material comprising a compound including a constitutional unit represented by Formula (1-1a):

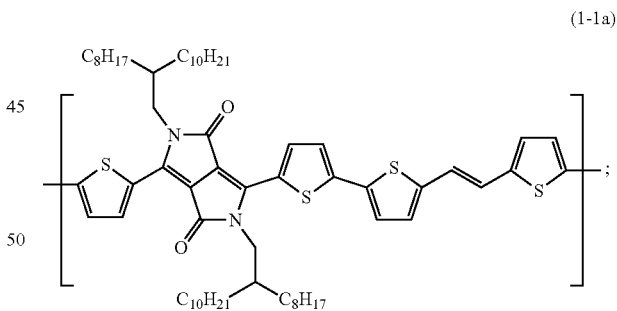

(1-1a)

with a solvent A comprising at least one selected from the group consisting of 2-methylcyclopentanone, 2-methylcyclohexanone, cyclohexyl methyl ether, and 2,3-dihydrobenzofuran.

* * * * *